United States Patent
Oliver et al.

[11] Patent Number: 6,120,752
[45] Date of Patent: Sep. 19, 2000

[54] MEDICINAL AEROSOL PRODUCTS CONTAINING FORMULATIONS OF CICLESONIDE AND RELATED STEROIDS

[75] Inventors: Martin J. Oliver, Clarendon Park; Kanu M. Fatania; John S. Scott, both of Loughborough, all of United Kingdom; Helgert Muller, Radolfzell, Germany

[73] Assignees: 3M Innovative Properties Company, St. Paul, Minn.; Byk Gulden Lomberg Chemische Fabrik GmbH, Konstanz, Germany

[21] Appl. No.: 09/076,958

[22] Filed: May 13, 1998

[30] Foreign Application Priority Data

May 21, 1997 [GB] United Kingdom ............ 9710496
Feb. 25, 1998 [GB] United Kingdom ............ 9803990

[51] Int. Cl.⁷ .............................................. A61K 9/12
[52] U.S. Cl. .............................. 424/45; 424/46; 514/826
[58] Field of Search ............... 424/45, 46; 514/826

[56] References Cited

U.S. PATENT DOCUMENTS

| 5,653,961 | 8/1997 | McNally et al. . |
| 5,653,962 | 8/1997 | Akehurst et al. . |
| 5,674,473 | 10/1997 | Purewal et al. . |

FOREIGN PATENT DOCUMENTS

| 0372777 | 6/1990 | European Pat. Off. . |
| 0553298 | 8/1993 | European Pat. Off. . |
| 195 41 689 | 5/1996 | Germany . |
| 2247680 | 3/1992 | United Kingdom . |
| 91/04011 | 4/1991 | WIPO . |
| 91/11173 | 8/1991 | WIPO . |
| 91/11495 | 8/1991 | WIPO . |
| 91/14422 | 10/1991 | WIPO . |
| 93/11743 | 6/1993 | WIPO . |
| 95/17195 | 6/1995 | WIPO . |
| 96/29985 | 10/1996 | WIPO . |

*Primary Examiner*—Raj Bawa
*Attorney, Agent, or Firm*—Ted K. Ringsred; MarySusan Howard; Robert W. Sprague

[57] ABSTRACT

A pharmaceutical aerosol formulation suitable for oral and/or nasal inhalation including an anti-inflammatory steroid of the formula

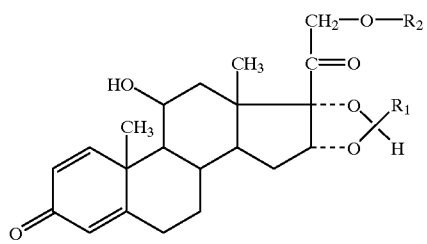

in which:

$R_1$ is 1-butyl, 2-butyl, cyclohexyl or phenyl and $R_2$ is acetyl or isobutanoyl, in particular ciclesonide. The formulations also include hydrofluorocarbon propellants such as HFC 134a and/or 227, and cosolvent such as ethanol in an amount sufficient to solubilize the ciclesonide or related steroid (and various optional ingredients, such as surfactant). The formulations exhibit very desirable physical and chemical stability, as well as excellent delivery characteristics.

8 Claims, 2 Drawing Sheets

MEDICINAL AEROSOL PRODUCTS CONTAINING FORMULATIONS OF CICLESONIDE AND RELATED STEROIDS

This application claims priority under 35 U.S.C. 119 to GB 9710496.2, filed May 21, 1997, and GB 9803990.2, filed Feb. 25, 1998.

FIELD

This invention relates to medicinal aerosol products and in particular to medicinal products containing a pregna-1,4, diene-3,20-dione-16-17-acetal-21 ester, suitable for administration by inhalation.

BACKGROUND

GB-2247680 discloses pregna-1,4-diene-3,20-dione-16-17-acetal-21 esters and their use in the treatment of inflammatory conditions.

The compounds have the general structure:

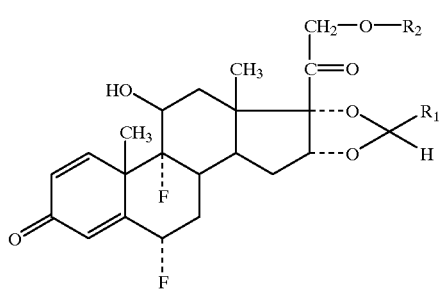

wherein $R_1$ is 2-propyl, 1-butyl, 2-butyl, cyclohexyl or phenyl; and $R_2$ is acetyl or isobutanoyl.

Ciclesonide is 11β, 16α, 17, 21-tetrahydroxypregna 1,4-diene-3,20-dione, cyclic 16,17-acetal with cyclohexanecarboxaldehyde, 21-isobutyrate having the structure of formula (I) without fluorine atoms and in which $R_1$ is cyclohexyl and $R_2$ is isobutanoyl. This compound has undergone evaluation as an antiasthmatic and pharmacokinetic studies show that it will be useful in an inhaler formulation. Ciclesonide is only moderately absorbed after oral administration and has low systemic activity. Concentration of the drug in the lungs is high and metabolism by liver oxidases is very high, giving the drug a low plasma half-life. Systemic activity of ciclesonide is three times lower than that of budesonide but anti-inflammatory activity is higher for the former.

GB-2247680 proposes a specific pressurized aerosol formulation for delivering ciclesonide for oral and nasal inhalation. The disclosed formulation consists of ciclesonide as a micronized suspension of particles, sorbitan trioleate surfactant, and a mixture of three CFC propellants: trichloro-fluoromethane, dichlorotetrafluoromethane, and dichlorodifluoromethane. However these CFC propellants are now believed to provoke the degradation of stratospheric ozone and there is a need to provide aerosol formulations for medicaments which employ so-called "ozone-friendly" propellants.

A class of propellants which are believed to have minimal ozone-depleting effects in comparison to conventional chlorofluorocarbons comprise hydrofluorocarbons and a number of medicinal aerosol formulations using such propellant systems are disclosed in, for example, EP 0372777, WO91/04011, WO91/11173, WO91/11495, WO91/14422, WO93/11743, and EP-0553298 (all hereby incorporated by reference). These applications are all concerned with the preparation of pressurised aerosols for the administration of medicaments and seek to overcome problems associated with the use of this new class of propellants, in particular the problems of stability associated with the pharmaceutical formulations prepared. The applications propose, for example, the addition of one or more of adjuvants such as alcohols, alkanes, dimethyl ether, surfactants (including fluorinated and non-fluorinated surfactants, carboxylic acids, polyethoxylates etc.).

However, despite the various approaches used in formulating drugs for use in aerosol inhalation, there are still many serious difficulties and uncertainties often encountered in attempting to develop a physically and chemically stable CFC-free formulation that reliably delivers an accurate dose of drug having the proper particle size range. In particular, there is a need for a CFC-free medicinal aerosol product containing ciclesonide (or similar molecules) that is chemically and physically stable and that is suitable for delivery to the respiratory system of a patient.

SUMMARY

It has now been surprisingly found that, rather than the prior art approach of formulating ciclesonide as a suspension, ciclesonide can be very beneficially formulated as a physically and chemically stable solution in formulations including hydrofluorocarbon propellants. According to the present invention there is provided a pharmaceutical composition comprising a therapeutically effective amount of a compound of the formula:

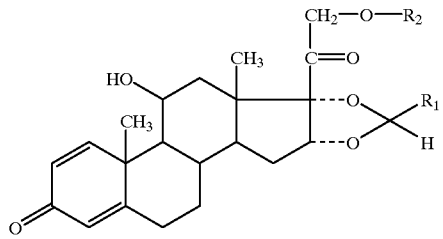

in which:

$R_1$ is 1-butyl, 2-butyl, cyclohexyl or phenyl and $R_2$ is acetyl or isobutanoyl, and a hydrofluorocarbon propellant, preferably selected from 1,1,1,2-tetrafluoroethane, 1,1,1,2,3,3,3-heptafluoropropane and a mixture thereof, and cosolvent, preferably ethanol, in an amount effective to solubilize the compound of formula (I) and optionally a surfactant.

The compounds of formula (I) is preferably ciclesonide and is generally present at a concentration of from 1 to 8 mg/ml, preferably 1 to 5 mg/ml.

The formulation generally comprises from 3 to 25% preferably 5 to 20%, more preferably 7 to 12% by weight ethanol.

The propellant preferably includes a hydrofluoroalkane, in particular Propellant 134a, Propellant 227 or a mixture thereof, generally at about 50:50 w/w. More preferably the propellant consists of Propellant 134a.

The formulations may contain surfactant but are preferably free of surfactant. The formulations are preferably free of other excipients.

Preferred formulations consist of from 1 to 5 mg/ml ciclesonide, 8% by weight ethanol and Propellant 134a.

The formulations may be prepared by adding the required quantity of drug into an aerosol vial, crimping a valve on the vial and introducing a pre-mixed blend of propellant and ethanol through the valve. The vial is placed in an ultrasonic bath to ensure solubilisation of the drug.

Alternatively, the formulations may be prepared by preparing a drug concentrate with ethanol and adding this concentrate to the pre-chilled propellant in a batching vessel. The resulting formulation is filled into vials.

The formulations may be filled in plastics, metal or glass vials. Suitable plastics materials include polyethyleneterephthalate; a preferred metal is aluminium.

The vials are equipped with a metered dose dispensing valve e.g. dispensing 50 μl with each actuation. A suitable metered dose dispensing valve comprises a valve ferrule having a rim and associated rim gasket for engaging the aerosol vial and an aperture therethrough;

a metering tank having walls defining an exterior, an internal metering chamber, an inlet orifice, an inlet end, and an outlet end;

an elongate valve stem having a filling channel, a filling end, a discharge end, and a discharge orifice;

wherein the outlet end of the metering tank is in sealing engagement with the valve ferrule, the discharge end of the valve stem passes through both the valve ferrule aperture and the outlet end of the metering tank and is in slidable sealing engagement with the valve ferrule;

wherein the filling end of the valve stem passes through and is in slidable engagement with the inlet orifice of the metering tank, and a bottle emptier surrounding the metering tank and filling end of the elongate valve stem and defining a passage between the metering tank and bottle emptier allowing communication between the inlet orifice of the metering tank and the aerosol vial;

wherein the valve stem is movable between an extended closed position wherein the filling channel of the valve stem allows open communication, via the inlet orifice, between the interior and the exterior of the metering chamber, and wherein the outlet end of the metering tank is closed, and a compressed open position wherein the inlet orifice of the metering tank is in ealing engagement with the filling end of the valve stem and the discharge orifice of the valve stem allows open communication between the interior and exterior of the metering chamber.

A suitable valve is commercially available under the trade name SPRAYMISER.

BRIEF DESCRIPTION OF THE DRAWINGS

The invention will now be described with reference to the accompanying drawings in which.

DETAILED DESCRIPTION

Figure 1:
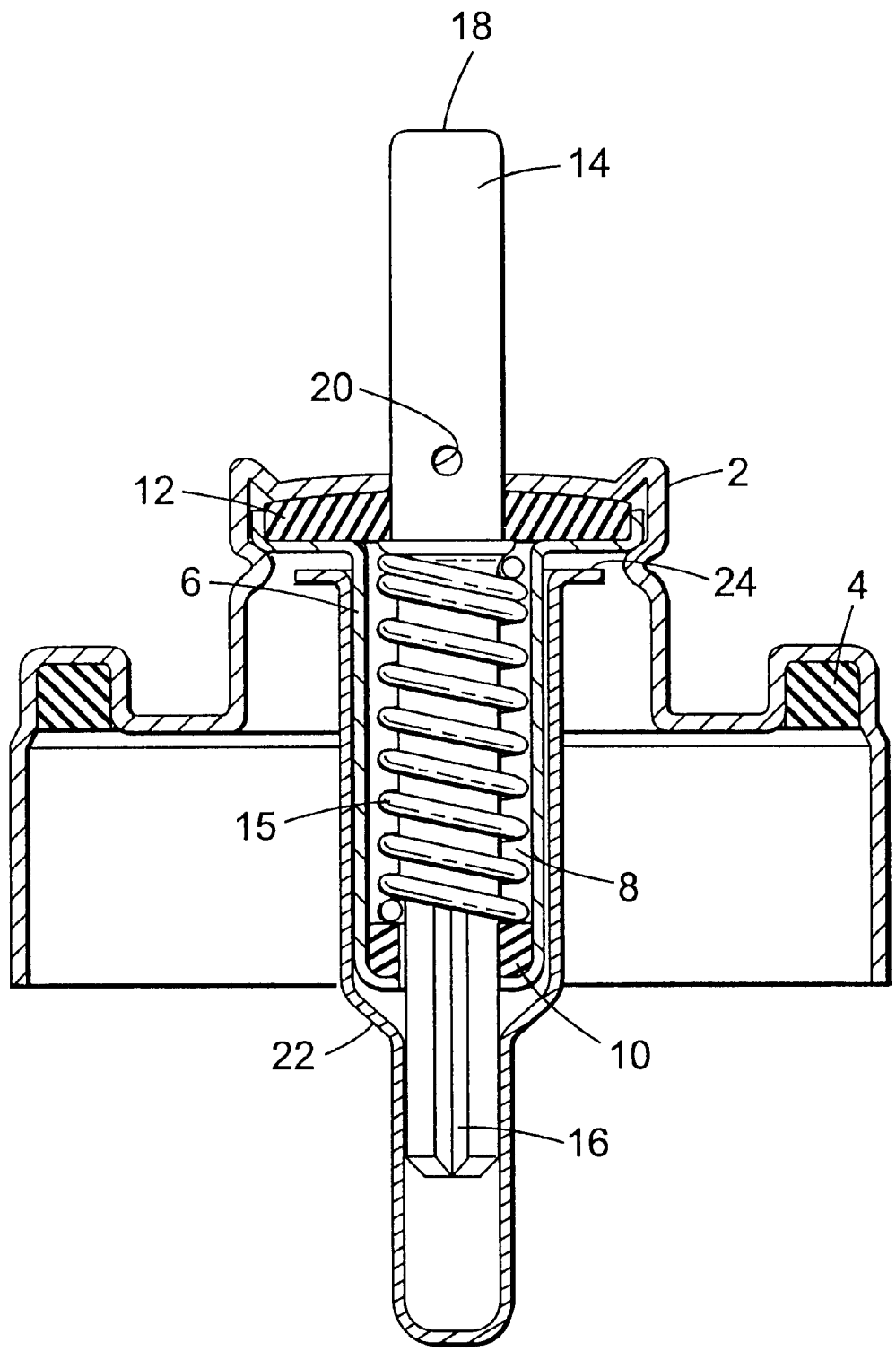
FIG. 1 represents a cross-section through a metered dose dispensing valve suitable for use in the invention.

The valve illustrated in FIG. 1 comprises a valve ferrule (2) and an associated rim gasket (4) for engaging an aerosol vial. The rim gasket (4) may conveniently comprise an ethylene-butylene copolymer e.g. the copolymer commercially available from Union Carbide under the trade name FLEXOMER GERS 1085NT.

A metering tank (6) has walls defining a metering chamber (8) having an inlet end associated with a tank seal (10) and an outlet end associated with a diaphragm (12). An elongate valve stem (14) having a filling channel (16), a discharge end (18) and a discharge orifice (20) extends through the valve ferrule and metering chamber in sealing engagement with the diaphragm (12) and tank seal (10).

The tank seal and diaphragm may conveniently comprise a butadiene-acrylonitrile copolymer e.g. Type DB-218 commercially available from American Gasket & Rubber Company.

A bottle emptier (22) surround the metering tank (6) and valve stem such that a capillary channel (24) is defined between the metering tank and bottle emptier to allow passage of aerosol formulation from the aerosol vial to the inlet end of the metering chamber.

The valve stem (14) is movable between an extended closed position wherein the filling channel (16) of the valve stem allows open communication, via the inlet orifice, between the interior and the exterior of the metering chamber, and wherein the outlet end of the metering tank is closed, and a compressed open position wherein the inlet orifice of the metering tank is in sealing engagement with the filling end of the valve stem and the discharge orifice of the valve stem allows open communication between the interior and exterior of the metering chamber. The valve stem (14) is biased to the extended closed position by spring (15).

Figure 2:
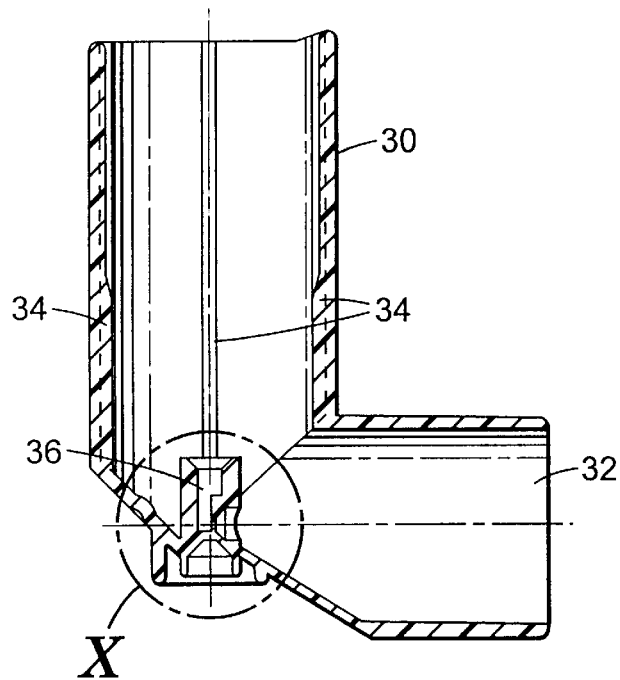
FIG. 2 represents a longitudinal cross-section through an adaptor for accommodating an aerosol vial equipped with a metered dose dispensing valve, in accordance with the invention.
Figure 3:
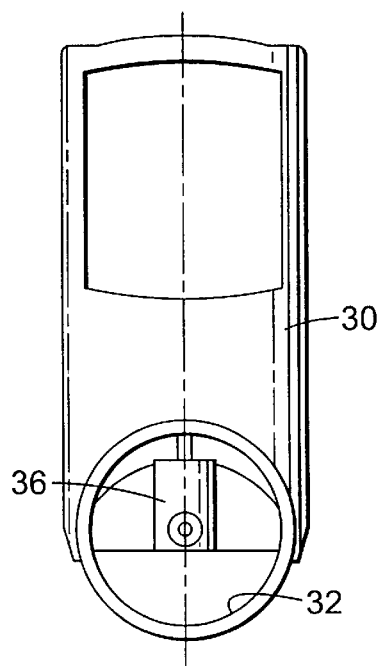
FIG. 3 represents a front view of the adaptor shown in FIG. 2, and, FIG. 4 represents a detailed section of the area X shown in FIG. 2.
Figure 4:
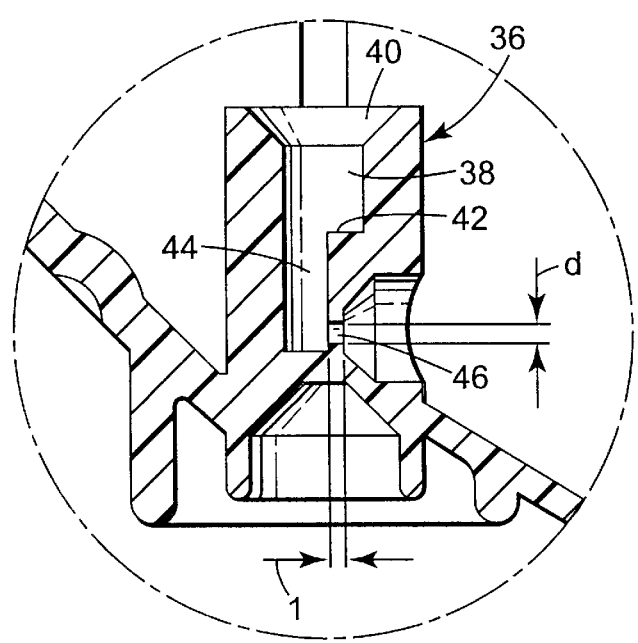

FIGS. 2 to 4 illustrate a press-and-breathe adaptor for an aerosol vial equipped with dispensing valve suitable for use in the invention. The adaptor comprises a body portion (30) and a mouthpiece (32). A plurality of ribs (34) are positioned within the body portion (30) in order to locate and support the aerosol vial (not shown) in the correct position. The dispensing end of the elongate valve stem of the metered dose dispensing valve is positioned within the nozzle block (36). The adaptor is made of polypropylene or high density polyethylene. However, to ensure a good seal between the valve stem (14) and the central aperture (38), high density polyethylene is preferred.

As shown in FIG. 4 the nozzle block (36) comprises a central aperture (38) having a flared opening (40) to accommodate the valve stem. The valve stem is inserted until it abuts the ledge (42). In use, the patient inserts the mouthpiece into the mouth and depresses the base of the aerosol vial while inhaling. The relative movement between the elongate valve stem and the metering tank causes the discharge orifice to enter the metering tank and the contents thereof are dispensed under pressure through the discharge end of the elongate valve stem to enter chamber (44) in the nozzle block (36) and exit through orifice (46). A plume of droplets of respirable size is directed from the orifice (46) into the mouthpiece (32) for inhalation by the patient.

It has been found that the dimensions of the orifice (46) may have a profound effect on the respirable fraction of the formulation dispensed from the mouthpiece of the adaptor. Both the jet length "l" and diameter "d" of the orifice (46) affect the delivery to the lung of the formulation. This is often assessed by an "in vitro" test which uses an Andersen Cascade Impactor, such as described in the U.S. Pharmacopoiea. An Andersen Respirable Dose is defined as the weight of drug delivered to plates 3 to 7 and the filter of the impactor from a single actuation of the inhaler. The optimum dimensions are also dependent upon the particular formulation to be dispensed. In general, medication delivery increases with increasing orifice diameter "d" and with increasing jet length "l". However, the Anderson respirable dose increases with decrease in orifice diameter "d".

The selection of particular dimensions of the nozzle orifice enables an Andersen Respirable Dose of greater than 120 micrograms to be achieved for a product delivering 200 micrograms of ciclesonide per actuation ex valve, without significantly detracting from the Medication Delivery. Thus the patient potentially derives the benefit of a higher than usual proportion of dispensed drug reaching the lungs without excessive build-up of drug on the actuator or the product falling short of regulatory stipulations.

For formulations containing from 5 to 10% by weight ethanol, particularly 8% by weight ethanol it has been found that good respirable doses are achieved with an orifice diameter "d" within the range 0.20 to 0.33 mm, preferably about 0.28 mm and a jet length "l" in the range 0.30 to 0.60 mm preferably 0.50 mm.

The invention will now be illustrated by the following Examples:

In each Example, the percentage of ethanol in the ethanol/propellant blend is denoted in brackets.

EXAMPLE 1

|  | mg/ml |
|---|---|
| Ciclesonide | 1.000 |
| Ethanol (5%) | 67.800 |
| P227 | 1287.200 |
|  | 1356.000 |

EXAMPLE 2

|  | mg/ml |
|---|---|
| Ciclesonide | 5.000 |
| Ethanol (5%) | 67.800 |
| P227 | 1283.200 |
|  | 1356.000 |

EXAMPLE 3

|  | mg/ml |
|---|---|
| Ciclesonide | 1.000 |
| Ethanol (20%) | 244.800 |
| P227 | 978.200 |
|  | 1224.000 |

EXAMPLE 4

|  | mg/ml |
|---|---|
| Ciclesonide | 5.000 |
| Ethanol (20%) | 244.800 |
| P227 | 974.200 |
|  | 1224.000 |

EXAMPLE 5

|  | mg/ml |
|---|---|
| Ciclesonide | 1.000 |
| Ethanol (7%) | 82.740 |
| P134a | 1098.260 |
|  | 1182.000 |

EXAMPLE 6

|  | mg/ml |
|---|---|
| Ciclesonide | 5.000 |
| Ethanol (7%) | 82.740 |
| P134a | 1094.260 |
|  | 1182.000 |

EXAMPLE 7

|  | mg/ml |
|---|---|
| Ciclesonide | 1.000 |
| Ethanol (20%) | 220.800 |
| P134a | 882.200 |
|  | 1104.000 |

EXAMPLE 8

|  | mg/ml |
|---|---|
| Ciclesonide | 5.000 |
| Ethanol (8%) | 220.800 |
| P134a | 878.200 |
|  | 1104.000 |

EXAMPLE 9

|  | mg/ml |
|---|---|
| Ciclesonide | 1.000 |
| Ethanol (8%) | 102.160 |
| P227 | 586.920 |
| P134a | 586.920 |
|  | 11277.000 |

EXAMPLE 10

|  | mg/ml |
|---|---|
| Ciclesonide | 5.000 |
| Ethanol (8%) | 102.160 |
| P227 | 584.920 |
| P134a | 584.920 |
|  | 11277.920 |

EXAMPLE 11

|  | mg/ml |
|---|---|
| Ciclesonide | 1.000 |
| Ethanol (12%) | 126.500 |
| P227 | 568.750 |
| P134a | 568.750 |
|  | 1265.000 |

EXAMPLE 12

|  | mg/ml |
|---|---|
| Ciclesonide | 5.000 |
| Ethanol (12oi) | 126.500 |
| P227 | 566.750 |
| P134a | 566.750 |
|  | 1115.000 |

EXAMPLE 13

|  | mg/ml |
|---|---|
| Ciclesonide | 1.000 |
| Ethanol | 94.800 |
| P134a | 1090.200 |
|  | 1186.000 |

EXAMPLE 14

|  | mg/ml |
|---|---|
| Ciclesonide | 2.000 |
| Ethanol | 94.7200 |
| P134a | 1089.280 |
|  | 1186.000 |

EXAMPLE 15

|  | mg/ml |
|---|---|
| Ciclesonide | 4.000 |
| Ethanol | 94.5600 |
| P134a | 1087.440 |
|  | 1186.000 |

EXAMPLE 16

|  | mg/ml |
|---|---|
| Ciclesonide | 4.000 |
| oleic acid | 0.237 |
| Ethanol | 94.541 |
| P134a | 1087.222 |
|  | 1186.000 |

All of the formulations of Examples 1 to 15 were clear, colourless solutions in which the ciclesonide was completely solubilized.

Examples 13 to 15 were the subject of stability trials over several months and proved to be physically and chemically stable.

Although the invention has been described in terms of preferred formulations and ingredients, it will be understood that these are not intended to be limiting. To the contrary, those skilled in the art will understand that various optional ingredients may be included, such as flavoring agents, preservatives, additional active ingredients, and the like, while still embodying the present invention.

We claim:

1. A pharmaceutical aerosol product comprising an aerosol vial equipped with a dispensing valve and containing an aerosol formulation suitable for oral or nasal inhalation comprising a therapeutically effective amount of a dissolved compound of the formula:

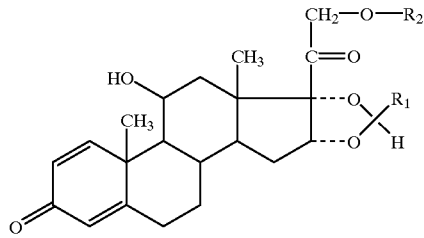

in which:

$R_1$ is 1-butyl, 2-butyl, cyclohexyl or phenyl and $R_2$ is acetyl or isobutanoyl, and a propellant selected from the group consisting of 1,1,1,2-tetrafluoroethane, 1,1,1,2,3,3,3-heptafluoropropane and a mixture thereof, and cosolvent in an amount effective to solubilize the compound of formula (I) and optionally a surfactant.

2. A pharmaceutical composition as claimed in claim 1 in which the valve is a metered dose dispensing valve.

3. A pharmaceutical composition as claimed in claim 2 in which the valve comprises a valve ferrule having a rim and associated rim gasket for engaging the aerosol vial and an aperture therethrough;

a metering tank having walls defining an exterior, an internal metering chamber, an inlet orifice, an inlet end, and an outlet end;

an elongate valve stem having a filling channel, a filling end, a discharge end, and a discharge orifice;

wherein the outlet end of the metering tank is in sealing engagement with the valve ferrule, the discharge end of the valve stem passes through both the valve ferrule aperture and the outlet end of the metering tank and is in slidable sealing engagement with the valve ferrule;

wherein the filling end of the valve stem passes through and is in slidable engagement with the inlet orifice of the metering tank, and a bottle emptier surrounding the metering tank and filling end of the elongate valve stem and defining a passage between the metering tank and bottle emptier allowing communication between the inlet orifice of the metering tank and the aerosol vial;

wherein the valve stem is movable between an extended closed position wherein the filling channel of the valve stem allows open communication, via the inlet orifice, between the interior and the exterior of the metering chamber, and wherein the outlet end of the metering tank is closed, and a compressed open position wherein the inlet orifice of the metering tank is in sealing engagement with the filling end of the valve stem and the discharge orifice of the valve stem allows open communication between the interior and exterior of the metering chamber.

4. A pharmaceutical product as claimed in claim 3 additionally comprising an adapter having a body for containing the aerosol vial, a nozzle block accommodating the discharge end of the valve stem and a mouthpiece.

5. A pharmaceutical product as claimed in claim 4 in which the nozzle block has an exit orifice directed towards the mouthpiece, the exit orifice having a diameter in the range 0.20 to 0.33 mm.

6. A pharmaceutical product as claimed in claim 5 in which the exit orifice has a diameter of about 0.28 mm.

7. A pharmaceutical product as claimed in claim 6 in which the exit orifice has a jet length in the range 0.30 to 0.60 mm.

8. A pharmaceutical product as claimed in claim 7 in which the exit orifice has a jet length of 0.50 mm.

* * * * *